US007221503B2

(12) United States Patent
Eberhardt et al.

(10) Patent No.: US 7,221,503 B2
(45) Date of Patent: May 22, 2007

(54) FAST MULTI-LINE LASER CONFOCAL SCANNING MICROSCOPE

(75) Inventors: Colin Eberhardt, Hartlepool (GB); Jafer Sheblee, Durham (GB); Ken Bell, North Shields (GB)

(73) Assignee: VisiTech International, Ltd., Sunderland (GB)

( * ) Notice: Subject to any disclaimer, the term of this patent is extended or adjusted under 35 U.S.C. 154(b) by 22 days.

(21) Appl. No.: 10/821,074

(22) Filed: Apr. 8, 2004

(65) Prior Publication Data

US 2005/0225850 A1    Oct. 13, 2005

(30) Foreign Application Priority Data

Apr. 8, 2003    (GB) .................................. 0308072.8

(51) Int. Cl.
    *G02B 21/06*    (2006.01)
(52) U.S. Cl. ........................ 359/385; 359/212; 359/305
(58) Field of Classification Search .................... None
    See application file for complete search history.

(56) References Cited

U.S. PATENT DOCUMENTS

| 4,499,437 | A | * | 2/1985 | Blazey | ........................ | 359/305 |
| 4,863,226 | A | * | 9/1989 | Houpt et al. | ................. | 359/212 |
| 6,867,899 | B2 | * | 3/2005 | Knebel | ........................ | 359/305 |
| 6,967,764 | B2 | * | 11/2005 | Birk | ........................... | 359/305 |
| 2002/0027709 | A1 | * | 3/2002 | Engelhardt et al. | .......... | 359/385 |
| 2002/0196535 | A1 | * | 12/2002 | Knebel et al. | ............... | 359/385 |

FOREIGN PATENT DOCUMENTS

WO    WO03012516 A1 *    2/2003

OTHER PUBLICATIONS

European Search Report (EP 04 00 8463.4-2217), dated Aug. 3, 2004, 6 pages.

* cited by examiner

*Primary Examiner*—Mark A. Robinson
*Assistant Examiner*—Lee Fineman
(74) *Attorney, Agent, or Firm*—Tarolli, Sundheim, Covell & Tummino, LLP

(57) ABSTRACT

According to a first embodiment the invention provides, for achieving fast multi-wavelength scanning in an acousto-optical deflector based confocal scanning microscope, dynamically adjusting an optical path of said an acousto-optical deflector based confocal microscope by mechanical means in accordance with a selected wavelength of a laser light beam, to compensate for astigmatism and collimation changes due to the change in input beam wavelength and modifying detected images of an object by electronic means to maintain alignment of the scan lines of the image at all wavelengths. According to a second embodiment the invention provides, for achieving fast multi-wavelength scanning in an acousto-optical deflector based laser confocal scanning microscope, dynamically adjusting drive parameters of the acousto-optical deflector in accordance with the selected wavelength of the input laser light beams, to maintain alignment of the scan lines of the image at all wavelengths. According to a third embodiment the invention provides, for achieving fast multi-wavelength scanning in an acousto-optical deflector based laser confocal scanning microscope dynamically adjusting drive parameters of the acousto-optical deflector in accordance with the selected wavelength of the input laser light beams, to maintain alignment of the scan lines of the image at all wavelengths, and mechanically pivoting the acousto-optical deflector about its central axis to compensate for the different deflection angles and ranges of the used illumination wavelengths.

16 Claims, 5 Drawing Sheets

Note that angular deflection is greatly exaggerated for clarity in the diagram.

FAST MULTI-LINE LASER CONFOCAL SCANNING MICROSCOPE

DESCRIPTION OF THE PRIOR ART

The inclusion of an acousto-optical deflector to produce the line scanning of a laser spot in a laser confocal microscope creates a unit which can operate with high speed and flexibility, i.e. with variable scanning amplitude, and suitable for various types of confocal microscopy. As a result of rapid line and frame scanning, it is then possible, in a very short space of time, to combine electronically a number of thin image sections to form an image with an increased depth of focus. Such collections of image sections are readily converted into a 3-Dimensional reconstruction of the original object volume, whereby spatial relationships between the object components can be rapidly visualised and measured.

FIG. 1 indicates an example of a laser scanning confocal microscope (100) in which an acousto-optical deflector is used to provide the line scanning of a laser spot. Such confocal laser scanning microscope is disclosed in EP-A-0 284 136 and its content is herewith included by reference.

A laser light beam 1 passes a beam expansion optical system 2 and 3, followed by a beam splitter 4, an acousto-optical deflector 5 having a planocylindrical lens 5.1 and a plano convex lens 5.2 both at the entrance and at the exit side, a lens 6, a deflector 7, which may be a mirror galvanometer, a lens 8, a quarter wave plate 16, and an objective 9 for focussing the laser beam 18 onto an object. In an object plane 10, an object, not shown, is further placed on a stationary object stage. The reflected light 19 traverses a return path identical to the outward path up to the beam splitter 4 after which it is split off to a polarising filter 11, a further objective 13, a spatial filter 14, a lens 17, a band pass or cut-off filter 12, and finally a detector 15.

FIG. 2 indicates another example of a laser scanning confocal microscope (200). A dichromatic mirror 20 has been incorporated in the light path between the planocylindrical lens 5.1 and the lens 6. Said mirror transmits the (short wave) laser light and deflects the long-wave return light originating, for example, from fluorescence. Note that a simple change in geometry will permit the use of a dichromatic mirror that reflects the (short wave) laser light and transmits the long-wave return light. This light is passed through a correction lens 21 and focussed with an objective 22 on a spatial filter 23 which is a slit filter, as a result of which this system has confocal characteristics. In this manner, a line detector is formed with a subsequent lens 24 and a detector 26. Between the lens 24 and the detector 26 one or more band pass or cut-off filters 25 has been incorporated which has the same function as that of the band pass or cut-off filter 12. With this embodiment, return light that has a wavelength other than that of the outward light can be advantageously examined if the acousto-optical deflector has too low an efficiency for said light, i.e. brings too large an attenuation.

BACKGROUND OF THE INVENTION

In biological objects that are autofluorescent, or have been labelled with fluorescent probes, a frequent requirement is to extract multi-spectral component images from the object that permit the spatial relationships between the variously labelled components to be studied. Living biological objects contain dynamic processes that may be fluorescently labelled so that, by repeating the same multi-spectral scan of the object, the temporal dynamics of these processes may also be studied. In all of these types of experiments it is important to have the ability to rapidly switch excitation wavelengths during the scanning process and the invention aims at providing a method of achieving fast multi-wavelength scanning in an acousto-optical deflector based laser confocal scanning microscope providing fast multi-wavelength scanning.

SUMMARY OF THE INVENTION

The present invention provides an acousto-optical deflector based laser confocal scanning microscope modified such that fast excitation wavelength switching produces images of the same sample area at all wavelengths and a method of achieving fast multi-wavelength scanning in an acousto-optical deflector based laser confocal scanning microscope while maintaining scanning of the same sample area at all wavelengths.

DESCRIPTION OF PREFERRED EMBODIMENTS

Figure 1:
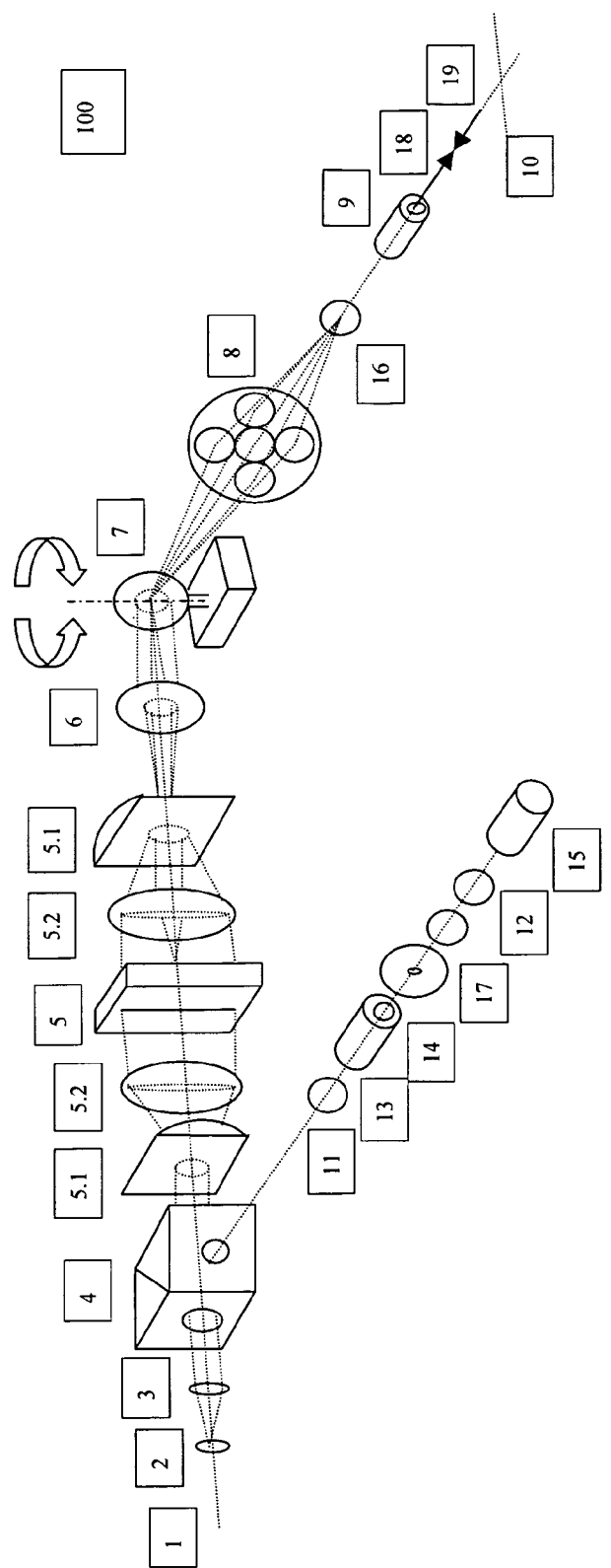
FIG. 1 indicates an example of a laser scanning confocal microscope in the prior art in which an acousto-optical deflector is used to provide the line scanning of a laser spot.

When an acousto-optical deflector is used as a deflection element in a scanning system there are a number of disadvantages that need to be considered.

As a result of the dispersive nature of the acousto-optical deflector, the return light of a wavelength (for example, fluorescence) other than the laser light no longer passes through the spatial filter. The spatial filter may be displaced by three piezo electric crystals, one for each of the three axes of the XYZ co-ordinate system and controlled in a manner that eliminates this effect.

Due to the time of transit across an acousto-optical deflector aperture of a change in the acoustic wave frequency, an acousto-optical deflector produces a cylindrical 'lensing' effect caused by the difference in deflection angles of the incident wavelength at the two ends of the acousto-optical deflector aperture. The difference in deflection angle between the ends of the acousto-optical deflector aperture increases with increased deflection scanning rates since the time of transit across the acousto-optical deflector aperture is constant.

The Bragg equation (wavelength=2×acoustic frequency×sin(deflection angle)) describes how the deflection angle is dependent on the wavelength of a light beam passing through an acousto-optical deflector. The absolute deflection angle and the difference in deflection angles of the light beam at the ends of the acousto-optical deflector aperture increase with increasing wavelength of the light beam when an oscillator driving the acousto-optical deflector follows a constant repetitive pattern of frequency sweeps.

Without attempts to correct for the lensing effects described above, changes in the wavelength of the illuminating light beam and changes in the rate of scanning will effect the position and size of the scanned area on the sample and also degrade the image quality due to the introduction of astigmatism in the optical path. The invention offers various methods of compensation for the lensing effect.

According to a first embodiment a method of achieving fast multi-wavelength scanning in an acousto-optical deflector based laser confocal scanning microscope according to the invention comprises dynamically adjusting an optical path of said an acousto-optical deflector based confocal microscope by mechanical means in accordance with a selected wavelength of a laser light beam, to compensate for astigmatism and collimation changes due to the change in input beam wavelength and modifying detected images of an object by electronic means to maintain alignment of the scan lines of the image at all wavelengths.

A laser confocal scanning microscope according to this embodiment of the invention comprises: means, including a laser light source, for emitting laser light beams at different wavelengths, such a source may include a tuneable laser and/or an array of lasers; a beam path, which may include a rigid or flexible optical light guide/optical fibre for coupling the laser light beam to the beam path, for directing said laser light beams from said laser light beam emitting means to an object stage for supporting an object, said beam path including a first deflector including an acousto-optical deflector for effecting line scanning, at least one objective for focussing the laser light beams onto the object on said object stage, a second deflector positioned between said acousto-optical deflector and said at least one objective, for effecting frame scanning, said second deflector and said at least one objective being positioned so that return light beams from the object follow the same beam path as the laser light beams focussed onto the object up to and including the second deflector, at least one detector positioned in the return light beam path downstream said second deflector, for detecting the return light beams from the object, the object being adapted to be scanned by the laser light beams from the laser light beam emitting means and measurements being adapted to be made with said at least one detector in order to obtain images of the object, and an electronic control and imaging system adapted to control the laser light beam emitting means to emit laser light beams of different selected wavelengths and adapted to dynamically adjust drive parameters of said acousto-optical deflector in accordance with the selected wavelength of the laser light beams, to maintain alignment of the scan lines of the image at all wavelengths. Such an electronic control and imaging system may be comprised of hard wired logic, a Digital Signal Processor, a microprocessor, a computer or a similar computational device.

A first embodiment thus describes compensation for the astigmatism and focus effects previously described using mechanical means to change the position of correction optical components within the optical path. An astigmatism lens (5.2 on the output side of the Acousto Optical Deflector) is moved in position to correct for astigmatism changes and a collimating lens (6) is moved to ensure that the beam entering a final objective is focussed by that objective to the same focal plane in the object being scanned. Remaining changes in the position of the image caused by the changes in scan line position on the object, due to deflection angle changes with wavelength changes, are compensated by using software pan, zoom and clipping of the recorded image data to maintain identical image size and position for all wavelengths.

Correction of the astigmatism and collimation by mechanical means is often too slow to enable the rapid switching of input beam wavelengths desired in biological research. For the study of dynamics in biological objects it is preferable to have wavelength switching on a scan line by scan line basis with scan line frequencies typically in the tens of kilohertz range.

According to a second embodiment a method of achieving fast multi-wavelength scanning in an acousto-optical deflector based laser confocal scanning microscope according to the present invention comprises an electronic control and imaging system adapted to dynamically adjust drive parameters of said acousto-optical deflector in accordance with a selected wavelength of a laser light beam, to maintain alignment of the scan lines of the image at all wavelengths.

A laser confocal scanning microscope according to this embodiment of the invention comprises: means, including a laser light source, for emitting laser light beams at different wavelengths, such a source may include a tuneable laser and/or an array of lasers; a beam path, which may include a rigid or flexible optical light guide/optical fibre for coupling the laser light beam to the beam path, for directing said laser light beams from said laser light beam emitting means to an object stage for supporting an object, said beam path including a first deflector including an acousto-optical deflector for effecting line scanning, at least one objective for focussing the laser light beams onto the object on said object stage, a second deflector positioned between said acousto-optical deflector and said at least one objective, for effecting frame scanning, said second deflector and said at least one objective being positioned so that return light beams from the object follow the same beam path as the laser light beams focussed onto the object up to and including the second deflector, at least one detector positioned in the return light beam path downstream said second deflector, for detecting the return light beams from the object, the object being adapted to be scanned by the laser light beams from the laser light beam emitting means and measurements being adapted to be made with said at least one detector in order to obtain images of the object, and an electronic control and imaging system adapted to control the laser light beam emitting means to emit laser light beams of different selected wavelengths and adapted to dynamically adjust drive parameters of said acousto-optical deflector in accordance with the selected wavelength of the laser light beams, to maintain alignment of the scan lines of the image at all wavelengths. Such an electronic control and imaging system may be comprised of hard wired logic, a Digital Signal Processor, a microprocessor, a computer or a similar computational device.

The second embodiment thus describes a method of achieving fast corrections for the lensing effect in an acousto-optical deflector enabling rapid switching of input beam wavelengths such that successive scans along a line in the object may be made at different wavelengths without reducing the scanning frequency.

The deflection range for a particular input beam is wavelength dependant, with longer wavelengths scanning over a wider range of deflection angles according to the Bragg equations. If an experiment requires the use of a wide range of illumination wavelengths the usable field of view can be constrained by this effect.

According to a third embodiment which is based on the first and second embodiments a method of achieving fast multi-wavelength scanning in an acousto-optical deflector based laser confocal scanning microscope according to the present invention comprises an electronic control and imaging system adapted to dynamically adjust drive parameters of said acousto-optical deflector in accordance with a selected wavelength of a laser light beam, to maintain alignment of the scan lines of the image at all wavelengths, and a mechanical pivoting of the acousto-optical deflector about its central axis to compensate for the different deflection angles and ranges of the used illumination wavelengths.

Figure 4:
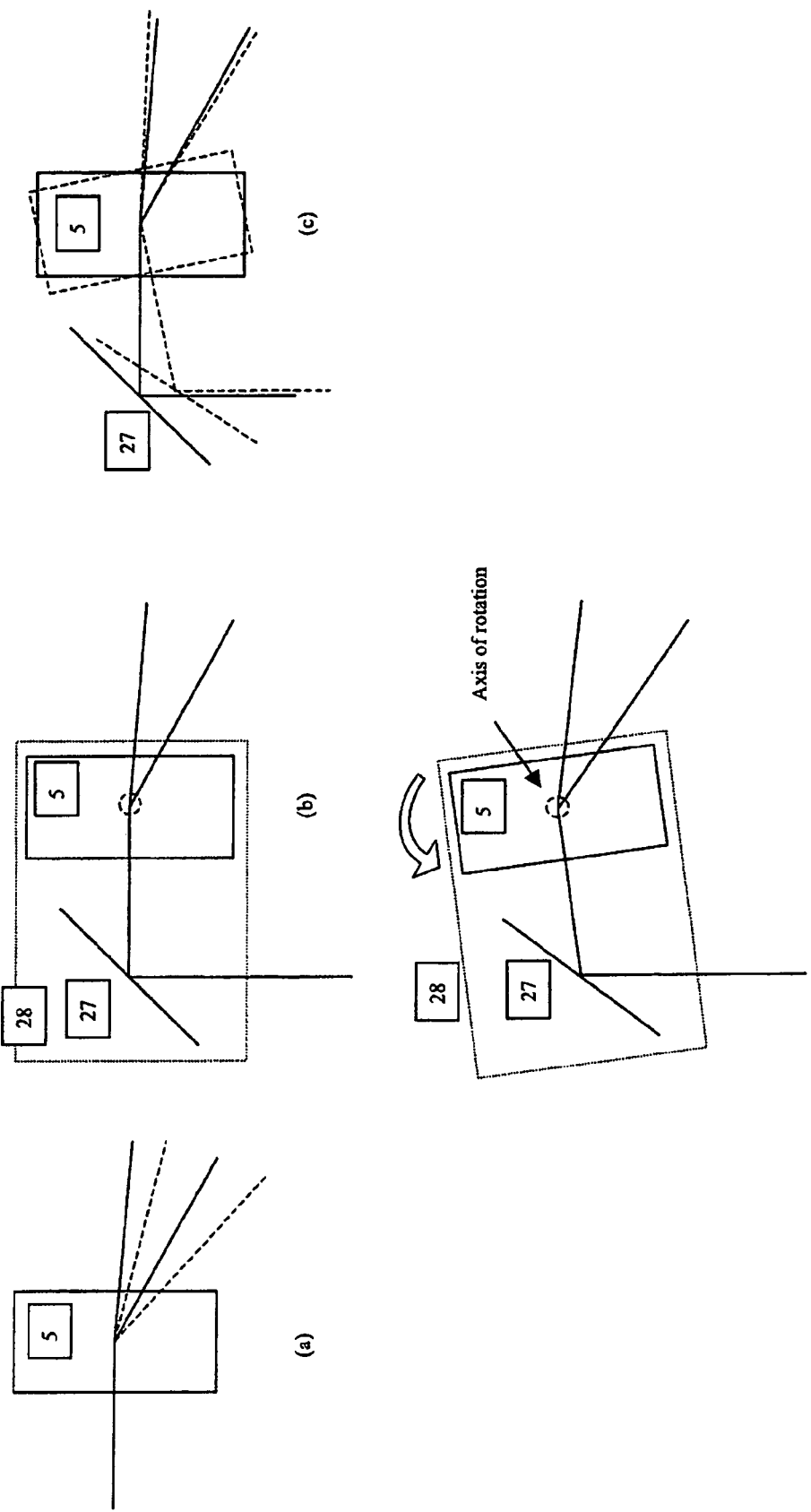
FIG. 4 is a diagram explaining the improvement in angular scan range when an Acousto-Optical-Deflector is mechanically rotated about its axis in accordance with the present invention.
Figure 5:
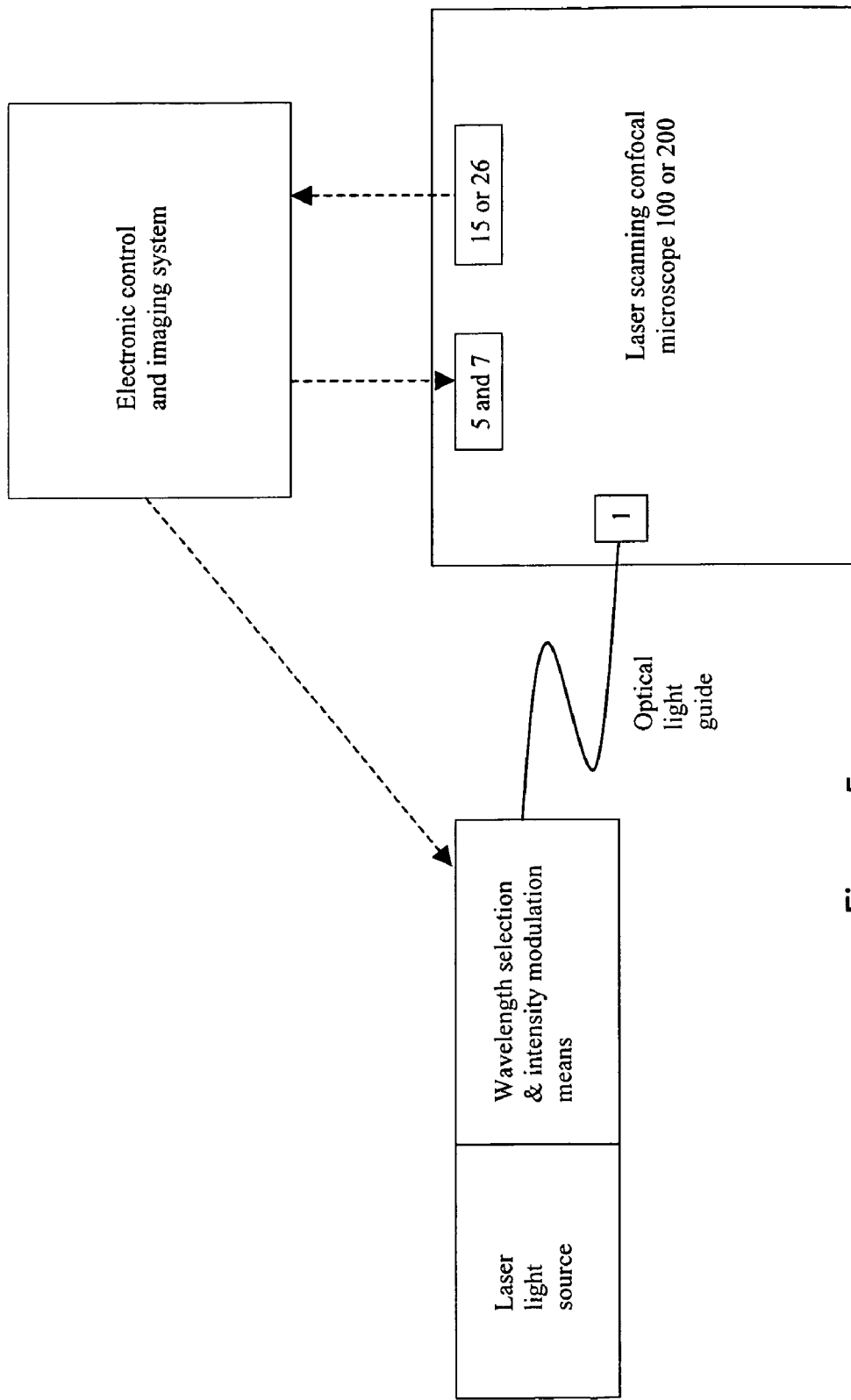
FIG. 5 shows the devices, peripheral to the laser scanning microscope, referenced in this invention.

A laser confocal scanning microscope according to this embodiment of the invention comprises in addition to the features of the first and second embodiment a mirror 27 positioned to direct the incident light into the input aperture of the acousto-optical deflector 5. The mirror 27 and the acousto-optical deflector 5 are mounted on a common base 28 and are arranged so that they may rotate together about the central axis of the acousto-optical deflector 5 as shown in FIG. 4. The central pivot axis of the acousto-optical deflector 5 is orthogonal to the plane in which the incident beam is deflected by the acousto-optical deflector.

The electronic control and imaging system of this embodiment is additionally adapted to control a mechanical means to effect the pivoting the acousto-optical deflector about the central pivot axis to re-align the scans at difference wavelengths.

The third embodiment thus describes a method of achieving fast corrections for the lensing effect in an acousto-optical deflector enabling rapid switching of input beam wavelengths such that successive scans along a line in the object may be made at different wavelengths without reducing the scanning frequency and a method for increasing the usable deflection range of the acousto-optical deflector over a range of illumination wavelengths by pivoting the acousto-optical deflector together with the mirror 27.

In the first embodiment mechanical means are used to move an astigmatism and a collimating lens to predetermined positions for each input beam wavelength by an electronic control system. Such mechanical means may be provided by electrical motors of various types, including AC, DC and stepper types, or by electromechanical actuators such as piezoelectric crystals. The position of the astigmatism lens has an almost linear relationship with the wavelength of the input beam as it corrects for the change in deflection angles due to changes in the wavelength of the input beam. The position of the collimating lens is determined experimentally for each wavelength as this lens compensates for any changes in focus from the changes in position of the compensating optical elements.

The electronic control system may also calculate control signals suitable for synchronising the selection of an input beam wavelength and also for synchronising an intensity modulation and/or blanking of the input beam during any chosen portion of the scanning pattern. Positional changes in the image are corrected by pan, zoom and clipping of recorded image data by software in an associated imaging system.

In the second embodiment an electronic control system provides dynamic control of the start frequency, end frequency and rate of frequency change of the drive signal to the acousto-optical deflector in such a way as to maintain constant line scanning position and a constant lensing effect at all input beam wavelengths.

From the Bragg equation it is known that to maintain the same deflection angle for any chosen input beam wavelength the acoustic grating spacing must change proportionally, this is effected by changing the frequency of an oscillator that drives the acousto-optical deflector. The drive oscillator frequency is swept over a range of values to effect the scanning of the laser beam along a line. Adjusting the range of the sweep frequencies in accordance with the Bragg equation for each input beam wavelength enables an identical line of spot positions to be scanned at any of these wavelengths.

The drive oscillator start and end frequencies are calculated from the known deflection characteristics of the acousto-optical deflector for the input beam wavelengths and are chosen dynamically to maintain an identical optical scan at each wavelength of the input beam, and hence maintain a constant lensing effect at each input beam wavelength. Thus the optical system may be optimised for one lensing condition, this condition being maintained dynamically for all scan rates and input beam wavelengths through software computer control of the acousto-optical deflector drive parameters.

To maintain an identical scan rate over identically positioned pixels in the scanned object for any input beam wavelength requires that the deflection angles of an acousto optical deflector at the start and end of each scan should be the same at all input beam wavelengths.

From the Bragg equation it is obvious that the deflection angle of the light passing through an acousto optical deflector increases directly in proportion to the wavelength of that light beam when the acoustic drive frequency and hence the acoustic wavelength are held constant.

If we define the maximum acoustic frequency available to drive the acousto-optical deflector (AOD) as providing the maximum deflection (corresponding to one, say right, edge of the scanned area) for the shortest light wavelength that must be deflected, and likewise define the minimum acoustic frequency available to drive the AOD as providing the minimum deflection (corresponding to the other, say left, edge of the scanned area) for the longest light wavelength that must be deflected, then any range of scanned line lengths, between the said left and right edges of the scanned area, can be duplicated at these or any intermediate wavelength. The acoustic frequencies necessary to provide a required scan line length and position within the said range at any other required wavelength can be calculated in proportion to the wavelength of the light to be deflected.

Figure 3:
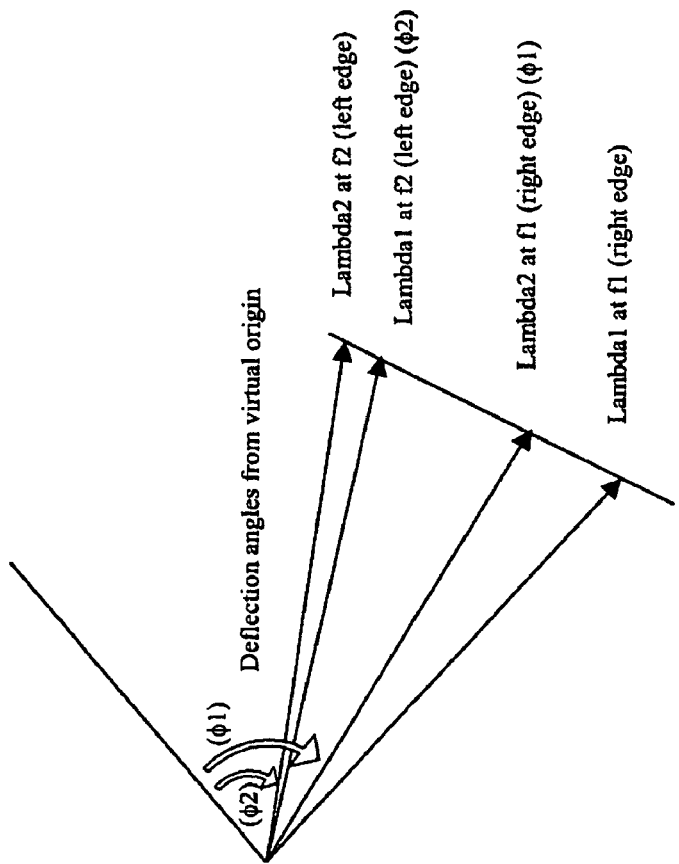
FIG. 3 is a diagram explaining the range of useable deflection angles available from an acousto-optical-deflector (AOD) used in a laser scanning confocal microscope in accordance with the present invention.

With reference to FIG. 3, lambda1 is the longest light wavelength to be deflected and lambda2 is the shortest light wavelength to be deflected. f1 is the maximum acoustic frequency available from an AOD driver oscillator and f2 is the minimum acoustic frequency available from the AOD driver oscillator.

At any intermediate light wavelength to be deflected (lambdaN), the deflection angle for the right edge (at acoustic frequency f1) is proportional to lambdaN/lambda2, and the deflection angle for the left edge (at acoustic frequency f2) is proportional to lambdaN/lambda1.

The range of useable deflection angles common to the range of light wavelengths lies between deflection angles 1 and 2. Therefore, the acoustic frequency to drive a chosen light wavelength lambdaN to the left edge is proportional to the ratio of (maximum wavelength lambda1/chosen wavelength lambdaN). Likewise, the acoustic frequency to drive a chosen light wavelength to the right edge is proportional to the ratio of (minimum wavelength lambda2)/(chosen wavelength lambdaN).

Knowledge of the input control voltage to acoustic drive frequency transfer characteristics of the drive oscillator for the AOD allows the electronic processor to calculate and output the scan control voltages necessary to create the required frequency sweeps that control the light beam deflection in the AOD. The electronic processor may also calculate control signals suitable for synchronising the selection of the input beam wavelength and also for synchronising the modulation or blanking of the input beam during any chosen portion of the scan waveform.

The invention offers the ability to control the position of the optical line scan very rapidly, enabling successive frame scans and even successive line scans to be made at different input beam wavelengths. This permits fast multi-colour scans to be made where input beam wavelengths are switched sequentially on repetitive scans of the same scan line and then repeating the same, or a different, sequence of input beam wavelengths on the next and subsequent scan lines. For even faster views of the sample under multicolour input beam scanning, the input beam wavelengths may be switched sequentially for adjacent scan lines, however this additional increase in image capture speed is gained at the loss of spatial resolution and registration of the images at each input beam wavelength.

In an advantageous embodiment a programmable voltage ramp generator drives a control input of a voltage controlled frequency oscillator that drives the acousto-optical deflector. Thus, defining the start voltage, the end voltage and the rate of voltage change of (typically) a classical sawtooth waveform, the programmable voltage ramp generator provides the appropriate oscillator signal to the acousto-optical deflector to scan the laser beam across the object. These voltage parameters can be altered dynamically at any time so that deflection changes due to changes in input beam wavelength can be compensated in the shortest practical time, limited only by the propagation speed of the acoustic wave in the acousto-optical deflector and the dimensions of the acousto-optical deflector aperture. These changes may synchronise, or be synchronised by, external events such as switching of the input beam wavelength. For example, an acousto optical tuneable filter (AOTF) at the output of a multi-line laser can be synchronised with the flyback period of the sawtooth waveform. Using an AOTF also provides a simple and efficient means of modulating or blanking of the laser intensity for the period of time during which the acousto-optical deflector drive signal is changing to a new scan condition, typically but not exclusively, during the flyback time at the commencement of a new scan line or a new scan frame. As acousto-optical deflectors (AOD's) also have the ability to modulate the intensity of the input light beam on its passage through the AOD, the AOD may also be used as a means to modulate and blank the input beam intensity.

In the third embodiment the electronic control system provides dynamic control of the start frequency, end frequency and rate of frequency change of the drive signal to the acousto-optical deflector in such a way as to maintain a constant lensing effect at all input beam wavelengths. The acousto-optical deflector and the beam incident upon its face are rotated about the central axis of the acousto-optical deflector thus increasing the overlap in scans between different illumination wavelengths.

With reference to FIG. 3, it can be seen that the resultant scan for wavelength Lambda1 scans a wider range of angles and has an angular offset when compared to the resultant scan for wavelength Lambda2 over the same acoustic frequency range. If an experiment requires the use of a wide range of illumination wavelengths the common scan range for all the illumination wavelengths must be used, thus resulting in a reduced overall scan range.

In order to increase the overlapping scan range the beam path through the acousto-optical deflector may be rotated about its central axis. In order to achieve this rotation the light incident upon the acousto-optical deflector 5 is directed by a mirror 27 oriented at 45 degrees to the input aperture of the acousto-optical deflector. This mirror is attached to the same mount 28 as the acousto-optical deflector 5 or connected directly or linked otherwise to the deflector and both may be pivoted about the centre axis of the acousto-optical deflector.

With reference to FIG. 4, Part (a) illustrates the original problem where light of two different wavelengths are deflected by the same range of acoustic frequencies resulting in two deflection ranges which are offset and differ in angular range with respect to each other. Part (b) illustrates a system whereby the light incident on the acousto-optical deflector is directed by a mirror. Rotation of the mount which incorporates both this mirror and the acousto-optical deflector results in an angular offset of the light exiting the acousto-optical deflector. Such mechanical means may be provided by electrical motors of various types, including AC, DC and stepper types, or by electromechanical actuators such as piezoelectric crystals. Part (c) illustrates how this rotation may be used to increase the overlap region of the two different wavelengths illustrated in Part (a).

With reference to FIG. 4, Part (c), it can be seen that the mechanical rotation of the mirror and the acousto-optical deflector results in an increase in the overlap region of the two different illumination wavelengths, however the overall scan range of each wavelength is not the same, hence a combination of mechanical rotation and an adjustment of the frequency sweeps for each wavelength, as utilised in the second embodiment, are required to execute the same scan with each illumination wavelength.

Figure 2:
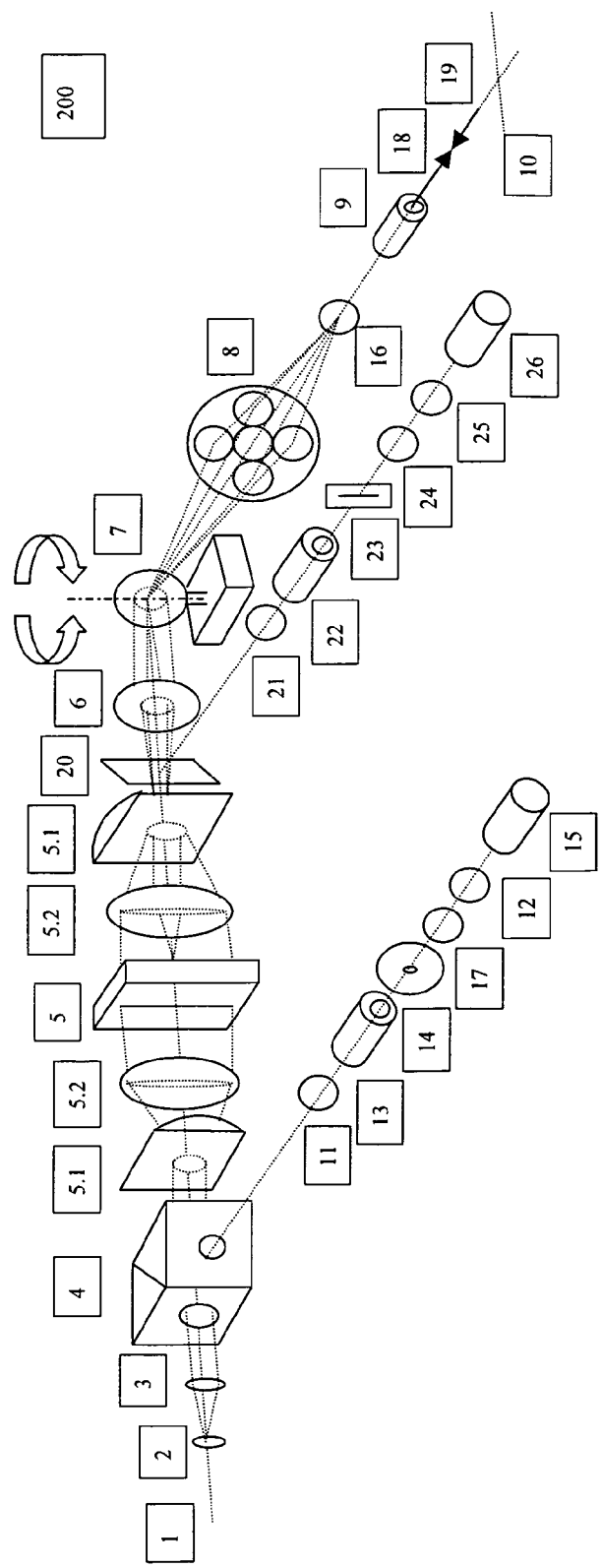
FIG. 2 indicates another example of a laser scanning confocal microscope in the prior art.

Any of the three embodiments described may be further adapted downstream from the separation of the return beam path from the input beam path by the beam-splitter (4) or the dichromatic mirror (20), to divide the return light beam path by means of additional beam splitters, dichromatic mirrors or combinations of both. Each resulting beam is adapted to be directed to one of a plurality of detectors, each detector having a spatial filter, objective, and lens duplicating the single detector beam path shown in the FIGS. 1 and 2, except that a bandpass or cut-off filter may be different for each detector path, therefore this plurality of detectors may be used to extract spectral information from the return light beam.

Additional advantages of this invention may also include the following: The scanned area of the object is identical for all wavelengths so there is no scanning of the object outside of the area of interest to cause photo-bleaching effects on adjacent areas of the object. Pixels taken from the same object at different input beam wavelengths have identical positions and dwell times which simplifies the application of the confocal microscope to such techniques as FRET (Fluorescence Resonance Energy Transfer, FLIM (Fluorescence Lifetime Imaging), FRAP (Fluorescence Recovery After Photobleaching), image ratioing etc.

What is claimed is:

1. A laser confocal scanning microscope comprising:
   means, including a laser light source, for emitting laser light beams at different wavelengths;
   a beam path for directing said laser light beams from said laser light beam emitting means to an object stage for supporting an object, said beam path including a first deflector including an acousto-optical deflector for effecting line scanning, at least one objective for focussing the laser light beams onto the object on said object stage, a second deflector positioned between said acousto-optical deflector and said at least one objective for effecting frame scanning, said second deflector and said at least one objective being positioned so that return light beams from the object follow the same beam path as the laser light beams focussed onto the object up to and including the second deflector, at least one detector positioned in the return light beam path downstream said second deflector for detecting the return light beams from the object, the object being adapted to be scanned by the laser light beams from the laser light beam emitting means and measurements being adapted to be made with said at least one detector in order to obtain images of the object, and an electronic control and imaging system adapted to control the laser light beam emitting means to emit individual laser light beams sequentially at selected wavelengths and adapted to dynamically adjust drive parameters of said acousto-optical deflector by dynamically controlling the start frequency and end frequency of the acousto-optical deflector in such a way as to maintain a constant line scanning position at all input beam wavelengths and dynamically controlling the rate of frequency change of the drive signal to the acousto-optical deflector in such a way as to obtain a constant lensing effect at all input beam wavelengths, to maintain alignment of the scan lines of the image at all wavelengths.

2. The laser confocal scanning microscope according to claim 1, further comprising:

a mirror positioned to direct the incident light into the input aperture of the said acousto-optical deflector, the mirror and acousto-optical deflector being mounted and arranged so that they may rotate about the central axis of the acousto-optical deflector, and said electronic control and imaging system is further adapted to dynamically adjust drive parmeters of said acousto-optical deflector and pivot said mirror and said acousto-optical deflector in accordance with the selected wavelength of the laser light beams, to increase the overlap in scan deflection angles between differing illumination wavelengths.

3. The laser confocal scanning microscope according to claim 1, said beam path further including:

a lens positioned between said objective and the second deflector to direct the light beams from said objective onto said second deflector, and at least one spatial filter positioned in the return light beam path between said second deflector and said at least one detector for effecting confocal imaging, whereby a frame-scanning movement introduced by said second deflector is adapted to be eliminated as a result of which the return light can be focussed on said at least one spatial filter.

4. The laser confocal scanning microscope according to claim 1, wherein a first beam splitter or dichromatic mirror is incorporated in the beam path between said acousto-optical deflector and said laser light beam emitting means so as to split off the return light beam and to direct it to said at least one detector, wherein said beam path is constructed such that the return light beam follows the same optical path as the laser light beam up to said first beam splitter or dichromatic mirror whereby the line scanning movement introduced by said acousto-optical deflector is eliminated.

5. The laser confocal scanning microscope according to claim 1, for use in fluorescence microscopy or other forms of microscopy in which the wavelength of the return beam differs from that of the laser light beams emitted from said laser light beam emitting means, wherein a spatial filter is mounted on an assembly of three piezoelectric crystals and can accordingly be moved in a 3D co-ordinate system, as a result of which the effect of the dispersive nature of the acousto-optical deflector on the return light of a different wavelength, which is deflected through an angle other than the reflected laser light, is eliminated and wherein a correspondingly matched bandpass or cut-off filter is incorporated in the return light beam path to filter out the reflected laser light.

6. The laser confocal scanning microscope according to claim 1, for use in fluorescence or other forms of microscopy in which the wavelength of the return beam differs from that of the laser light beam, wherein a dichromatic mirror is incorporated in the beam path between the acousto-optical deflector and the second deflector in order to deflect the return light beam with differing wavelengths downstream of the second deflector and to direct it via an objective and a subsequent spatial filter to a subsequent detector, the subsequent spatial filter being a slit filter which forms a line detector with the subsequent detector.

7. The laser confocal scanning microscope according to claim 6, wherein the return light beam is adapted to be divided into a plurality of light beams by means of an additional beam splitter or dichromatic mirror or a plurality of additional beam splitters or dichromatic mirrors inserted into the return beam path after the return beam path is separated from the input beam path by the first beam splitter or dichromatic mirror, each resulting beam is adapted to be directed to one or more detectors, each detector having a spatial filter, objective, and lens duplicating the single detector beam path, except that a bandpass or cut-off filter may be different for each detector.

8. The laser confocal scanning microscope according to claim 1, wherein said electronic control and imaging system is adapted to provide synchronisation of the selected laser light beam wavelength to the flyback or other selected time point in the line scans by applying control signals to a wavelength selection means mounted downstream of said laser light source such that the laser light beams passing through said wavelength selection means on their passage into or through the beam path are controlled such that only the selected wavelength is permitted to pass through the beam path.

9. The laser confocal scanning microscope according to claim 8, wherein said wavelength selection means comprises an acousto-optical tuneable filter (AOTF).

10. The laser confocal scanning microscope according to claim 1, wherein said electronic control and imaging system is adapted to provide synchronisation of the intensity modulation or blanking of the laser light source beam to the flyback or other selected time point in the line scans by applying control signals to an intensity modulation means mounted downstream of said laser light source such that the laser light beams passing through said intensity modulation means on their passage into or through the beam path are controlled such that the intensity of the light beams can be modulated or blanked.

11. The laser confocal scanning microscope according to claim 10, wherein said intensity modulation means comprises an acousto-optical tuneable filter (AOTF) and/or said acousto-optical deflector.

12. The laser confocal scanning microscope according to claim 1, wherein said electronic control and imaging system is comprised of hard wired logic, a Digital Signal Processor, a microprocessor, a computer or a similar computational device.

13. The laser confocal scanning microscope according to claim 1, wherein said laser light source includes a multi-line laser, a tuneable laser, and/or an array of lasers emitting at various wavelengths and an optical configuration that provides collinear laser beams.

14. The laser confocal scanning microscope according to claim 1, wherein said second deflector comprises a mirror galvanometer.

15. The laser confocal scanning microscope according to claim 1, wherein the light beams are coupled to the beam path by means of a rigid or flexible optical light guide.

16. The laser confocal scanning microscope according to claim 15, wherein the optical light guide is an optical fibre.

* * * * *